United States Patent [19]

Kishimoto et al.

[11] Patent Number: 5,288,722
[45] Date of Patent: Feb. 22, 1994

[54] 6-AMINO-6-DESOXYFUMAGILLOLS, PRODUCTION AND USE THEREOF

[75] Inventors: Shoji Kishimoto, Takarazuka; Shogo Marui, Suita; Takeshi Fujita, Takarazuka, all of Japan

[73] Assignee: Takeda Chemical Industries, Ltd., Osaka, Japan

[21] Appl. No.: 762,658

[22] Filed: Sep. 19, 1991

Related U.S. Application Data

[63] Continuation of Ser. No. 489,370, Mar. 6, 1990, abandoned.

[30] Foreign Application Priority Data

Mar. 6, 1989 [JP] Japan ................ 1-53535

[51] Int. Cl.⁵ .............. A61K 31/40; A61K 31/445; A61K 31/335; C07D 303/02
[52] U.S. Cl. .................. 514/278; 514/409; 514/444; 514/462; 514/475; 544/70; 544/230; 546/15; 546/207; 548/147; 548/407; 548/300.7; 549/332; 549/551; 549/554; 549/563; 549/60
[58] Field of Search ............ 544/70, 230; 548/147, 548/301, 336, 407; 546/15, 207; 549/332, 551, 554, 563, 60; 514/278, 409, 444, 462, 475

[56] References Cited

FOREIGN PATENT DOCUMENTS 1918794 11/1969 Fed. Rep. of Germany .

OTHER PUBLICATIONS

J. A. DiPaolo, et al., Antibiotics Annual (1958–1959), pp. 541–546.

Journal of American Chem. Society, vol. 83, pp. 3096–3113 (1961).
The Journal of Antibiotics, vol. 41, pp. 999–1008 (1988).
Chemical Abstract, 106:176153y, 1987.

*Primary Examiner*—C. Warren Ivy
*Assistant Examiner*—Ba K. Trinh
*Attorney, Agent, or Firm*—David G. Conlin; David S. Resnick

[57] ABSTRACT

The present invention relates to a compound of the formula:

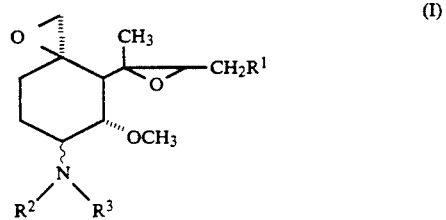

(I)

wherein $R^1$ is 2-methyl-1-propenyl group or isobutyl group; $R^2$ and $R^3$ are each hydrogen atom, an optionally substituted hydrocarbon residue or an optionally substituted acyl group or $R^2$ and $R^3$ may form a ring together with the adjacent nitrogen atom; and the bonding mark ~ represents an α-linkage or β-linkage, or a salt thereof. The compound (I) of the present invention has, among others, angiogenesis inhibiting activity, cell-growth inhibiting activity and immune reaction inhibiting activity, thus being useful as medicines, etc.

8 Claims, No Drawings

6-AMINO-6-DESOXYFUMAGILLOLS, PRODUCTION AND USE THEREOF

This is a continuation of copending application Ser. No. 07/489,370 filed on Mar. 6, 1990, now abandoned.

FIELD OF INVENTION

The present invention relates to novel 6-amino-6-desoxyfumagillols and salts thereof having an activities of inhibiting, among others, angiogenesis, cell-proliferation and immune reactions, and having therapeutic and prophylactic activities against, for example, various inflammatory diseases (rheumatic diseases, psoriasis, etc.), diabetic retinopathy, arteriosclerosis, tumors and rejection symptoms in the case of internal organ transplantation.

BACKGROUND OF INVENTION

Angiogenesis is deeply concerned with occurrence or pathological processes of various inflammatory diseases (rheumatic diseases, psoriasis, etc.), diabetic retinopathy, tumors, etc. Therefore, it has been considered that inhibition of angiogenesis has a connection with therapy and prophylaxis of these diseases and several research groups have searched for substances capable of inhibiting angiogenesis. For example, mention is made of research works for application of Protamine by Taylor [Taylor, S. et al., Nature, 297, 307 (1982)] and for use of heparin in the presence of cortisone by Folkman et al. [Folkman, J. et al., Science, 221, 719 (1983)]. Furthermore, patent applications have been filed directed to ascorbic acid ether and its related compounds (JP-A-131978/1983) or polysaccharide sulfate DS4152 (JP-A-119500/1988) as compounds showing activity of inhibiting angiogenesis. However, the activities of these compounds are not sufficiently satisfactory, and compounds having more satisfactory activity desired.

Cell-proliferation is a function indispensable for for growth and maintenance of living organisms. In higher animals, various tissues or organs have specific proliferation mechanisms which are controlled by various controlling substances. In recent years, numerous substances capable of positively controlling cell-proliferation, i.e., "cell-proliferation factors", have been isolated and purified. In addition, it has been made clear that these factors perform an important role in ontogeny and maintenance of life. On the other hand, there are many reports disclosing that abnormal cell-proliferation, especially when such proliferation is out of the control, is related with various diseases. Examples of such diseases include, tumors and arteriosclerosis.

Further, it has been discovered that various cell-proliferation factors participate in activation of immunocompetent cells, especially lymphocytes. Excess production or excess response of these cell-proliferation factors is considered to be one of the factors of aggravating autoimmune diseases or allergic diseases. Therefore, the use of medicines showing actions of selectively inhibiting cell-proliferation factors, controlling responses to cell-proliferation factor and of immunosuppression is considered to provide effective means of prophylaxis and therapy of these diseases, and also of suppressing graft rejection in internal organ transplantation.

OBJECTS OF THE INVENTION

The object of the present invention lies in providing novel compounds having, among others, actions of inhibiting angiogenesis, suppressing cell-proliferation and immunosuppression.

For attaining the above-mentioned object, the present inventors have conducted searches for various compounds and evaluation of them. As a result, it was found that 6-amino-6-desoxyfumagillol chemically, derived from fumagillin which has been known as an antibiotic agent and an antiprotozoal agent, and its related compounds have superb actions of inhibiting angiogenesis, suppressing cell-proliferation and immnosuppression, thus the present invention has been accomplished.

SUMMARY OF THE INVENTION

The present invention relates to the compound represented by the formula,

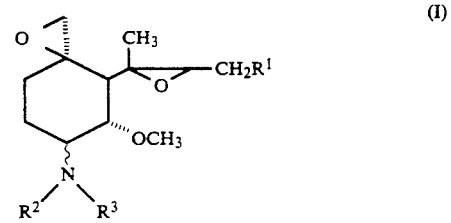

(I)

wherein $R^1$ is 2-methyl-1-propenyl group or isobutyl group; $R^2$ and $R^3$ are each hydrogen atom, an optionally substituted hydrocarbon residue or an optionally substituted acyl group or $R^2$ and $R^3$ may form a ring taken together with the adjacent nitrogen atom; the bonding mark ~ represents an α-linkage or β-linkage, or a salt thereof, production and use thereof.

DETAILED DESCRIPTION OF THE INVENTION

Examples of the hydrocarbon residues of the optionally substituted hydrocarbon residues shown by $R^2$ or $R^3$ include aliphatic hydrocarbon residues (straight-chained or branched alkyl groups, alkenyl groups, alkynyl groups or cycloaliphatic hydrocarbon residues) and aromatic hydrocarbon residues (e.g. aryl groups), and, among others, alkyl groups or aryl groups are especially preferable.

Examples of the acyl groups of the optionally substituted acyl groups- shown by $R^2$ or $R^3$ include various organic or inorganic residual groups bonded via carbonyl group or sulfonyl group (e.g. alkanoyl group, aroyl group, aromatic heterocyclic carbonyl group, carbamoyl group, benzenesulfonyl group, alkyl sulfonyl group, thiocarbamoyl group, alkoxy carbonyl, phenoxy carbonyl group, etc.).

Above all, preferable examples of $R^2$ are hydrogen atom, optionally substituted alkyl group or aryl group, and those of $R^3$ are hydrogen atom, optionally substituted acyl group groups or alkyl groups as above.

Preferable embodiments of the above-mentioned $R^2$ and $R^3$ are as follows.

Examples of optionally substituted alkanoyl groups shown by $R^3$ include amino, lower alkyl amino (e.g. methylamino, ethylamino, isopropylamino, etc.), di-lower alkyl amino (e.g. dimethylamino, diethylamino, etc.), nitro, halogen (e.g. fluorine, chlorine, bromine, iodine, etc.), hydroxyl, lower alkylthio, lower alkoxy (e.g. methoxy, ethoxy, etc.), cyano, carbamoyl, carboxyl, lower alkoxycarbonyl (e.g. methoxycarbonyl, ethoxycarbonyl, etc.), carboxy lower alkoxy (carboxymethoxy, 2-carboxyethoxy, etc.), optionally substituted phenyl, aromatic heterocyclic groups (preferably 5-6 membered aromatic heterocyclic groups containing 1-4 hetero-atoms such as nitrogen, oxygen, sulfur, etc., such as 2-furyl, 2-thienyl, 4-thiazolyl, 4-imidazolyl, 4-pyridyl, etc.), and, preferably, alkanoyl groups having 1-4 substituents (preferably, unsubstituted alkanoyl groups having 2 to 20 carbon atoms, such as formyl, acetyl, propionyl, isopropionyl, butyryl, pentanoyl, hexanoyl, heptanoyl, octanoyl, nonanoyl, lauroyl, undecanoyl, myristoyl, palmitoyl, stearoyl, arachinoyl, etc.). Among them, acetyl, butyryl, octanoyl, 3-carboxylpropionyl and 4-carboxybutyryl are preferable.

Examples of the optionally substituted aroyl groups shown by $R^3$ include benzoyl, 1-naphthoyl, 2-naphthoyl, etc. optionally having 1 to 3 substituents such as $C_{2-6}$ lower alkyl such as ethyl, propyl etc., amino, halogen (e.g. fluorine, chlorine, bromine, etc.), hydroxyl, lower alkoxy (e.g. methoxy, ethoxy, etc.), cyano, carbamoyl, carboxyl, etc. Among them, benzoyl and 2-carboxybenzoyl are preferable.

Examples of the substituents in the optionally substituted aromatic heterocyclic carbonyl groups shown by $R^3$ include the same substituents as those of the above-mentioned substituted aroyl group. As the aromatic heterocyclic carbonyl groups, use is made of 5- or 6-membered ones containing 1 to 4 hetero atoms such as nitrogen, oxygen, sulfur, etc., and, among them, 2-furoyl, 2-thenoyl, nicotinoyl and isonicotinoyl are preferable.

The optionally substituted carbamoyl groups shown by $R^3$ include carbamoyl group, mono-substituted carbamoyl group and di-substituted carbamoyl group, and substituents of them are exemplified by lower alkyl (e.g. methyl, ethyl, propyl, butyl, etc.), lower alkanoyl (preferably $C_{1-6}$, e.g. acetyl, propionyl, etc.), lower halogenoalkanoyl (e.g. chloroacetyl, trichloroacetyl), lower alkoxy carbonyl methyl (e.g. methoxy carbonyl methyl, ethoxy carbonyl methyl, etc.), carboxy methyl, optionally substituted phenyl, naphthyl, benzoyl, substituents forming cyclic amino group (e.g. pyrrolidino, piperidino, morpholino, piperazino, 4-methylpiperazino, 4-phenylpiperazino, etc.), taken together with the nitrogen atom of the carbamoyl group. Among them, chloroacetyl, phenyl and benzoyl are preferable.

As the optionally substituted alkyl group shown by $R^2$ and $R^3$, mention is made of $C_{1-20}$ straight-chain or branched alkyl groups, which may optionally be substituted with 1 to 3 substituents same as those in the above-mentioned optionally substituted alkanoyl groups, and the said alkyl group may be epoxidated at an optional position. Among them, methyl, ethyl and benzyl are preferable.

Examples of substituents of the optionally substituted benzenesulfonyl group shown by $R^3$ include lower alkyl (e.g. methyl, ethyl, etc.), halogen (fluorine, chlorine, bromine, etc.), and one to three of these substituents may be located at optional positions of the benzene ring.

Examples of optionally substituted alkylsulfonyl groups shown by $R^3$ include $C_{1-6}$ lower alkyl sulfonyl groups optionally having one to three of the same substituents as those of the above-mentioned optionally substituted alkanoyl groups. Among them, methyl sulfonyl and ethyl sulfonyl are preferable.

The optionally substituted thiocarbamoyl groups shown by $R^3$ include thiocarbamoyl group, mono-substituted thiocarbamoyl group and di-substituted carbamoyl group. As the substituents, mention is made of the same substituents as those of the above-mentioned optionally substituted carbamoyl groups.

As the optionally substituted alkoxycarbonyl groups shown by $R^3$, mention is made of, for example, straight-chain or branched lower $(C_{1-6})$alkoxycarbonyl groups which may have 1 to 3 substituents which are the same as those of the above-mentioned optionally substituted alkanoyl groups. Among them, are preferable methoxy carbonyl ethoxy carbonyl, propoxy carbonyl, butoxy carbonyl, isobutoxy carbonyl and 1-chloroethoxy carbonyl.

Examples of the substituents of optionally substituted phenoxycarbonyl groups shown by $R^3$ include the same substituents of the above-mentioned optionally substituted benzenesulfonyl groups, and one to three of these substituents may be substituted at optionally positions of phenoxy group.

Examples of the optionally substituted aryl groups shown by $R^2$ include phenyl, 1-naphthyl and 2-naphthyl, which are optionally substituted with one to three of the same substituents as those of the above-mentioned optionally substituted aroyl groups.

In the present specification, examples of the substituents of optionally substituted phenyl groups include lower alkyl (e.g. methyl, ethyl, propyl, butyl, etc.), lower alkoxy (e.g. methoxy, ethoxy, propoxy, etc.), halogen (e.g. fluorine, chlorine, bromine, etc.), halogenated alkyl (e.g. trifluoromethyl, chloromethyl, etc.), nitro, etc., and one to five of these substituents may be substituted at optional positions of the phenyl ring.

And, in the present specification, unless otherwise specified, the lower alkyl group means $C_{1-6}$ straight-chain or branched alkyl groups, and the lower alkoxy group means $C_{1-6}$ alkoxy groups.

When the compound (I) of this invention has in its molecule an acidic substituent (e.g. carboxyl or the like) or a basic substituent (e.g. amino, lower alkylamino, di-lower alkylamino or the like), it can be used as a pharmacologically acceptable salt. As the pharmacologically acceptable salts, use is made of salts with inorganic bases, salts with organic bases, salts with basic or acid amino acid, or the like. As inorganic bases capable of forming these salts, use is made of, for example, an alkali metal (e.g. sodium, potassium, etc.), an alkaline earth metal (e.g. calcium, magnesium, etc.), etc.; as organic bases, use is made of trimethylamine, triethylamine, pyridine, picoline, N,N-dibenzylethylenediamine, ethanolamine, diethanolamine, tris-hydroxymethylaminomethane, dicyclohexylamine, etc.; as inorganic acids, use is made of, for example, hydrochloric acid, hydrobromic acid, sulfuric acid, nitric acid, phosphoric acid, etc.; as organic acids, use is made of, for example, formic acid, acetic acid, trifluoroacetic acid, oxalic acid, tartaric acid, fumaric acid, maleic acid, methanesulfonic acid, benzenesulfonic acid, p-toluenesulfonic acid, etc.; and, as basic or acid amino acids, use is made of, for example, arginine, lysine, ornithine, aspartic acid, glutamic acid, etc. Of these salts, those with bases (i.e. salts with inorganic bases, salts with organic bases, salts with basic amino acids) mean salts which can be formed with the carboxyl group in the substituents of compound (I), and, salts with acids (i.e. salts with inorganic acids, salts with organic acids, salts with acid amino acids) mean salts which can be formed with the amino group, lower alkylamino group, di-lower alkyl-amino group, etc. in the substituents of the compound (I).

The salts also include quaternary ammonium salts in which the $-NR^2R^3$ portion is in the following formula: $-NR^2R^3R^8 \cdot X^-$ wherein $R^8$ is lower alkyl or phenyl-lower alkyl, such as methyl, ethyl and X is an anion, such as halogen.

A compound of the general formula (I), wherein $R^1$ is 2-methyl-1-propenyl group, and $R^2$ and $R^3$ are both hydrogen atom, i.e. 6-amino-6-desoxyfumagillol is the compound derived from fumagillol which is the hydrolysate of fumagillin produced by a microorganism [Tarbell, D. S. et al., Journal of American Chemical Society, 83, 3096 (1961)], and, as shown by the formulae (II) and (III), it exists as two types of compounds, i.e. 6α-amino-desoxyfumagillol and 6β-amino-6-desoxyfumagillol. These two types of compounds are different from each other in the absolute structure of 6-position amino group, and the 6-position amino group of 6α-amino-6-desoxyfumagillol shown by the formula (II) has the same absolute structure as the 6-position hydroxyl group of fumagillol. The object compound (I) of the present application include compounds shown by the formulae (II) and (III) and their related compounds.

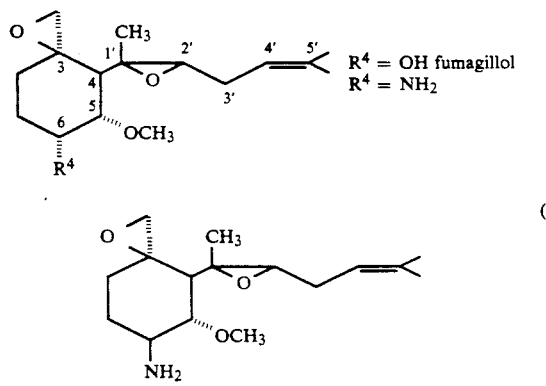

And, the compound (I) has, in its molecule, besides the above-mentioned 6-position, asymmetric center at 3-position, 4-position, 5-position and 1'-position and 2'-position on the side chain at 4-position, but its absolute structure is based on the starting fumagillol and in agreement with the absolute structure of fumagillol.

6α-Amino-6-desoxyfumagillol (II) is can be obtained by subjecting fumagillol to oxidation by the method described in publication of JP-A-476/1987 to give 6-oxo-6-desoxyfumagillol(6-dehydrofumagillol), which is then subjecting to reduction with a metal hydride such as sodium cyanoborohydride in the presence of ammonium acetate. And, using primary amine instead of ammonium acetate, the reduction is conducted while keeping the pH of the reaction mixture neutral to weakly acidic to give directly an N-mono-substituted derivative of the compound (II). On the other hand, by employing catalytic reduction using, for example, palladium-carbon as the catalyst, in place of the reduction using metal hydride, the double bond on the side chain at 4-position is also reduced at the same time, and 4',5'-dihydro compound of the compound (II) can be obtained.

6β-Amino-6-desoxyfumagillol (III) is obtained by subjecting fumagillol to Mitsunobu reaction using diethyl azodicarboxylate and triphenylphosphine and phthalimide or succinimide [Mitsunobu, O., Synthesis, 1981, p.1] to give 6β-imido compound, then allowing hydrazine or methyl hydrazine to react with the 6β-imido compound, followed by processing with an acid.

Production of the compound (I), wherein $R^1$ is isobutyl group, $R^2$ and $R^3$ are both hydrogen atom, can be accomplished by subjecting 4',5'-dihydro compound obtained by catalytic reduction of fumagillol under usual conditions (e.g. using 5% palladium-carbon in a methanol solution) to the same reaction as described above.

The compound (I), wherein $R^2$ or $R^3$ is, both or either one, a substituent other than hydrogen atom, can be produced, using a compound (II) or its N-mono-substituted compound, a compound (III), and 4',5'-dihydro compounds of them as starting materials, by subjecting them to acylation, carbamoylation, thiocarbamoylation, alkylation or sulfonylation by, for example, the method described below, or by isolating the intermediates in those reactions. And, when $R^2$ or $R^3$ is a group which does not change by catalytic reduction, 6-(N-substituted amino)-6-desoxyfumagillol is subjected to catalytic reduction to convert into 6-(N-substituted amino)-4',5'dihydro-6-desoxyfumagillols. When the acylating agent, carbamoylating agent, thiocarbamoylating agent, acylating agent and sulfonylating agent have a substituent such as amino, hydroxyl, carboxyl etc., these substituents are preferably protected, and the protecting groups are selected in accordance with the stability of the product. Preferable examples of the protecting groups are, in the case of amino, 4-nitrobenzyloxycarbonyl, 2-trimethylsilylethoxycarbonyl, etc., and in case of hydroxyl, 4-nitrobenzyl, are t-butyl dimethylsilyl, etc., and, in case of carboxyl, are 4-nitrobenzyl, etc. For deprotection, a conventional means such as catalytic reduction or use of fluoride ion is employed. Additionally stating, in cases of carbamoylation and alkylation, it is possible that a lower alkyl such as methyl, ethyl, etc. is used as the protecting group of the carboxyl group, then, after the reaction, the protecting group is removed by hydrolysis under mild alkaline conditions.

1) Acylation

This acylation is conducted by allowing a reactive derivative of activated carboxylic acid such as acid anhydride, acid halide, active amide, active ester, active thioester, etc. to react with 6-amino-6-desoxyfumagillol, 6-amino-4',5'-dihydro-6-desoxyfumagillol or their N-alkyl or N-monoaryl substituted compounds (hereinafter referred to simply as starting amine).

Namely, the acylation is usually conducted by such reaction as shown by the following scheme:

Reactive derivative of $R^5OH$ + starting amine ⟶

Compound (I)
[$R^3 = R^5$]

(wherein $R^5$ stands for (1) optionally substituted alkanoyl group, (2) optionally substituted aroyl group and (3) optionally substituted aromatic heterocyclic carbonyl group defined for $R^2$ and $R^3$).

Such reactive derivatives as above are set forth specifically as follows.

1) Acid halide

For example, acid chloride, acid bromide or the like are employed.

2) Acid anhydride

For example, mono-lower alkyl carbonate mixed acid anhydride or the like is employed.

3) Active amide

Amides with, for example, pyrazole, imidazole, 4-substituted imidazole, dimethyl pyrazole, benzotriazole, or the like are employed.

4) Active ester

Besides such esters as methoxymethyl ester, benzotriazol ester, 4-nitrophenyl ester, 2,4-dinitrophenyl ester, trichlorophenyl ester and pentachlorophenyl ester, esters with, for example, 1-hydroxy-1H-2-pyridone, N-hydroxysuccinimide or N-hydroxyphthalimide.

5) Active thioester

Thioesters with a heterocyclic thiol such as 2-pyridyl thiol, 2-benzothiazolyl thiol, etc. are employed.

Said reactive derivative of carboxylic acid is used usually in an amount of about 1 to 10 times mol., preferably 1 to 5 times mol., relative to 1 mol. of the starting amine. And, in a case of using the carboxylic acid in the free state, the reaction is conducted preferably in the presence of a condensing agent. Examples of the condensing agent to be used include N,N'-dicyclohexylcarbodiimide, N-cyclohexyl-N'-morpholinoethylcarbodiimide, N-cyclohexyl-N'-(4-diethylaminocyclohexyl)carbodiimide, N-ethyl-N'-(3-dimethylaminopropyl)carbodiimide, etc.

This reaction is carried out usually in the presence of a base. Examples of the base include tertiary amine such as diisopropylethylamine, tributylamine, triethylamine, pyridine, picoline, N,N-dimethylaminopyridine, N-methylmorpholine, N-methylpiperidine, etc., alkali metal hydrogencarbonates such as sodium hydrogencarbonate, potassium hydrogencarbonate, etc., alkali metal carbonates such as potassium carbonate, sodium carbonate, etc., alkali metal hydrides such as sodium hydride, potassium hydride, etc., organic metals such as butyl lithium, lithium diisopropylamide, etc., and the amount of the base to be added usually ranges from about 1 mol. to 10 times mol. relative to 1 mol. of the starting amine.

This reaction is conducted usually in an organic solvent which does not exert undesirable effects on the reaction. Examples of the organic solvent which does not exert undesirable effects on the reaction include amides such as dimethylformamide, dimethylacetamide, etc., halogenated hydrocarbons such as dichloromethane, chloroform, 1,2-dichloroethane, etc., ethers such as diethylether, tetrahydrofuran, dioxane, etc., esters such as methyl acetate, ethyl acetate, isobutyl acetate, methyl propionate, etc., nitriles such as acetonitrile, propionitrile, etc., nitro compounds such as nitromethane, nitroethane, etc., ketones such as acetone, methyl ethyl ketone, etc., aromatic hydrocarbons such as benzene, toluene, etc., and these may be used singly or as a mixture of two or more species in a suitable ratio. And, the tertiary amine employed as the base may be used as the solvent simultaneously.

The reaction temperature varies with the amounts, kinds, etc. of carboxylic derivatives, bases and solvents, and ranges from −80° C. to 100° C., preferably from 0° C. to room temperatures (in this specification, room temperatures mean temperatures ranging from about 20° to about 35° C., unless otherwise specified). The reaction time ranges from about 30 minutes to about 5 days.

2) Alkylation

This alkylation is conducted by allowing a starting amine to react with an alkylating agent, for example alkyl halide represented by the formula $R^6Y$ [wherein $R^6$ stands for an optionally substituted alkyl groups in the definition of $R^3$ and Y stands for a leaving group (e.g. halogen (chlorine, bromine, iodine, etc.))], dialkyl sulfate (e.g. methyl sulfate, diethyl sulfate, etc.). This alkylating agent is used in an amount of usually about 1 to 5 times mol. relative to the starting amine.

This reaction is conducted usually in the presence of a base. As the base, use is made of afore-mentioned alkali metal hydrogencarbonates, alkali metal carbonates, alkali metal hydrides, organic metals, etc., and the amount to be added ranges from about 1 to 5 times mol. relative to the starting amine.

This reaction is carried out usually in an organic solvent which does not exert undesirable influence on the reaction. Examples of such organic solvents include afore-mentioned amides, halogenated hydrocarbons, ethers, esters, nitriles, nitro-compounds, ketones and aromatic hydrocarbons, and these solvents can be used singly or as a mixture of two or more species of them in a suitable ratio.

The reaction temperature varies with the amounts, kinds etc., of alkylating agents, bases and solvents, and it ranges from −80 to 100° C., preferably from 0° C. to room temperatures. The reaction time ranges from about 20 minutes to about 5 days.

Use of alkyl dihalide as the alkylating agent affords 6-(cyclic amino)-6-desoxyfumagillols. Thus obtained product can be led to an ammonium type derivative by further allowing to react with alkyl halide (cf. Example 20).

The said alkylation is also conducted by allowing 6-amino-6-desoxyfumagillol or its 4′,5′-dihydro compound to react with ketone or aldehydes under reductive conditions, i.e. catalytic reduction. Preferable catalysts for the reduction are exemplified by palladium-carbon, palladium black, Raney nickel, etc. The reaction is conducted in an alcohol (e.g. methanol, ethanol, etc.), ether (e.g. tetrahydrofuran, dimethoxyethane, etc.) or a mixture of such a solvent as above with water in the presence of hydrogen gas, at temperatures ranging from ice-cooling to about 80° C., preferably around room temperatures.

The reduction can be conducted by using a metal halide, preferably sodium borohydride or sodium cyano borohydride.

The reaction is carried out preferably in a solvent, for example alcohol (e.g. methanol, ethanol), ether (tetrahydrofuran, dimethoxyethane), nitrile (e.g. acetonitrile) or an aqueous mixture thereof, and, more desirably, the reaction is conducted while maintaininq the pH of the reaction mixture at weakly acid side, (about pH 3 to 6), and, for adjusting the pH, a buffer solution or a mineral acid (e.g. hdyrochloric acid), an organic acid (e.g. acetic acid) or an aqueous solution thereof is added.

The amount of a metal halide to be used varies with the starting material and kinds of carbonyl compounds employed, and it ranges from a little excess to about 100 times relative to the theoretical amount, preferably a little excess to about 10 times, and, depending on cases, as the reaction proceeds, it may be supplemented in a suitable amount.

The reaction temperature ranges from about −20° C. to 80° C, preferably from about 0° C. to 30° C.

3) Carbamoylation

Carbamoylation for introducing a mono-substituted carbamoyl group is carried out by usually allowing isocyanate to react with the starting amine, as, for example, shown by the following reaction scheme.

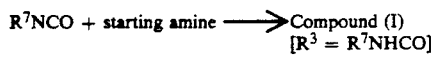
$$R^7NCO + \text{starting amine} \longrightarrow \text{Compound (I)}$$
$$[R^3 = R^7NHCO]$$

(wherein $R^7$ stands for a substituent of the optionally substituted carbamoyl group shown by $R^3$ such as lower alkyl, lower alkanoyl chloroacetyl, etc.). The isocyanate is used in an amount of usually about 1 mol to 5 times mol. relative to 1 mol. of the starting amine.

This reaction is carried out usually in the presence of a base. As the base, use is made of above-mentioned tertiary amine, alkali metal hydrogencarbonates, alkali metal carbonates, alkali metal hydrides, organic metals, etc., and the amount of such a base as above to be added ranges from about 1 mol. to 5 times mol. relative to the starting amine.

This reaction is carried out usually in an organic solvent which does not exert undesirable influence on the reaction. Examples of such organic solvents as above include afore-mentioned amides, halogenated hydrocarbons, ethers, esters, nitriles, nitro-compounds, ketones and aromatic hydrocarbons, and these solvents can be used singly or as a mixture of two or more species of them in a suitable ratio. The tertiary amine employed as the base may be used as the solvent simultaneously.

The reaction temperature varies with the amounts and kinds of isocyanate, the base and the solvent then employed, and usually ranges from about $-80°$ C. to $100°$ C., preferably from $0°$ C. to room temperatures. The reaction time ranges from about one hour to about five days.

Among the compounds having mono-substituted carbamoyl group thus obtained, compounds having, for example, chloroacetylcarbamoyl, trichloroacetylcarbamoyl, etc., can be converted to compounds having carbamoyl group by removing chloroacetyl group or trichloroacetyl group by a conventional process (e.g. at room temperatures or an elevated temperatures under basic conditions).

The said carbamoylation can also be conducted by allowing the starting amine to react with carbamoyl halide.

The said carbamoyl halide is used in an amount of usually 1 mol. to 5 times mol. relative to 1 mol. of the starting amine. This reaction is carried out usually in the presence of a base. As the base, use is made of the above-mentioned tertiary amine, alkali metal hydrogencarbonates, alkali metal carbonates, alkali metal hydrides, organic alkali metals, etc., and the amount of the base to be added ranges from about 1 mol. to 5 times mol. relative to the starting amine.

This reaction is carried out usually in an organic solvent which does not exert undesirable influence on the reaction. Examples of such organic solvents as above include afore-mentioned amides, halogenated hydrocarbons, ethers, esters, nitriles, nitro-compounds, ketones and aromatic hydrocarbons, and these solvents can be used singly or as a mixture of two or more species of them in a suitable ratio. The tertiary amine employed as the base may be used as the solvent simultaneously.

The reaction temperature varies with the amounts and kinds of carbamoyl halide, bases and solvents, and it ranges from about $0°$ C. to around reflux temperatures of the reaction medium, preferably from about $25°$ C. to reflux temperature.

The said carbamoylation can also be carried out by allowing the starting amine to react with chloroformic ester (e.g. phenyl chloroformate, ethyl chloroformate, isobutyl chloroformate, chloroformic acid 1-chloroethyl, etc.) or 1,1'-carbonyl diimidazole to give an active ester, followed by allowing the ester to react with primary or secondary amine. The said chloroformic esters or 1,1'-carbonyl diimidazole and amines are used in an amount of usually ranging from 1 mol. to 5 times mol. relative to one mol. of the starting amine.

In this reaction, the reaction between the starting amine and chloroformic ester is carried out in the presence of a base. As the said base, use is made of the above-mentioned tertiary amine, alkali metal hydrogencarbonates, alkali metal carbonates, alkali metal hydrides, organic alkali metals, etc. The amount of the base to be added ranges usually from about 1 mol. to 5 times mol. relative to 1 mol. of the starting amine.

This reaction is carried out usually in an organic solvent which does not exert undesirable influence on the reaction. Examples of such organic solvents as above include afore-mentioned amides, halogenated hydrocarbons, ethers, esters, nitriles, nitro-compounds, ketones and aromatic hydrocarbons, and these solvents can be used singly or as a mixture of two or more species of them in a suitable ratio. The reaction temperature varies with the amounts and kinds of the chloroformic esters, bases, amines and solvents, and it ranges from $-20°$ C. to the reflux temperature of the reaction medium, preferably from $0°$ C. to $50°$ C. Incidentally, the active esters obtained as intermediates are also included in the compounds (I) which are the object compounds of the present application.

4) Thiocarbamoylation

In the above carbamoylation, by using isothiocyanate in place of isocyanate, a derivative into which a mono-substituted thiocarbamate group is introduced can be synthesized by the same reaction as mentioned above. The reaction is shown by, for example, the following scheme.

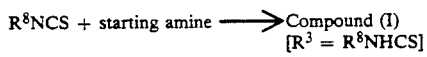
$$R^8NCS + \text{starting amine} \longrightarrow \text{Compound (I)}$$
$$[R^3 = R^8NHCS]$$

[wherein $R^8$ stands for a substituent of optionally substituted thiocarbamoyl group, which is the same as in the definition of $R^3$].

5) Sulfonylation

The sulfonylation is conducted by allowing an activated sulfonic acid derivative, for example, sulfonic anhydride, sulfonic halide (e.g. sulfonyl chloride, sulfonyl bromide, etc.) to react with the starting amine.

More specifically, the reaction is performed as shown by the following scheme.

Reactive derivative of $R^9OH$ + starting amine $\longrightarrow$

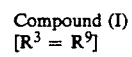
Compound (I)
$[R^3 = R^9]$

[wherein $R^9$ stands for an optionally substituted benzene sulfonyl group, which is the same as in the definition of $R^3$, or an optionally substituted alkyl sulfonyl group, which is the same as in the definition of $R^3$].

The reactive derivative of the sulfonic acid is, generally, used in an amount of about 1 to 5 times mol. relative to 1 mol. of the starting amine.

This reaction is usually conducted in the presence of a base. As the base, use is made of the aforementioned tertiary amine, alkali metal hydrogencarbonates, alkali metal carbonates, alkali metal hydrides, organic metals, etc., and the amount thereof to be added is, generally, about 1 to 10 times mol. relative to 1 mol. of fumagillol.

This reaction is conducted usually in an organic solvent which does not exert an undesirable effect on the reaction. Examples of organic solvents exerting no undesirable effect on the reaction include the aforementioned amides, halogenated hydrocarbons, ethers, esters, nitriles, nitro compounds, ketones, and aromatic hydrocarbons, and these can be employed singly or as a mixture of two or more species of them in a suitable ratio. And, the tertiary amine employed as the base can be used also as the solvent.

The reaction temperature varies with amounts and kinds of the sulfonic acid derivative, base and solvent then employed, but it usually ranges from $-80°$ C. to $100°$ C., preferably from $0°$ C. to room temperatures. The reaction time ranges from one hour to about 5 days.

Thus-produced 6-amino-6-desoxy fumagillol and related compounds (I) can be isolated by known separating and refining means (e.g. chromatography, crystallization), etc.

The compounds of this invention show actions of, among others, inhibiting angiogenesis, cell-proliferation and immune reactions, and are useful as therapeutic and prophylactic agents of various inflammatory diseases (rheumatic diseases, psoriasis), diabetic retinopathy, arteriosclerosis, tumors and rejection symptoms in the case of internal organ transplantation. And, they can be safely administered orally or non-orally as they are or a pharmaceutical composition prepared by mixing with known [pharmaceutically acceptable carriers, excipients, etc. e.g. tablets, capsules (including soft capsules, microcapsules), liquids, injections, suppositories]. The dosage varies with, among others, subjects, routes and symptoms, but, usually, it ranges, in adults, from about 0.1 mg/kg to about 40 mg/kg body weight, preferably from about 0.5 mg/kg to about 20 mg/kg body weight per day.

EXPERIMENTAL EXAMPLE 1

The object compounds (I) obtained in the Working Examples given below were evaluated for angiogenesis inhibitory activity by the rat cornea micropocket method. The data obtained are summarized in Table 1.
Method of evaluation Essentially the same method of Gimbrone et al. [J. National Cancer Institute, 52, 413-419 (1974)] was followed. Thus, adult male Sprague-Dawley rats 11 to 16 week old) were anesthetized with nembutal and locally anesthetized by instillation of xylocaine eyedrops onto the eyeball. The cornea was incised to a length of about 2 mm inside from the corneal circumference by means of an injection needle, and a sustained release pellet containing basic fibroblast growth growth factor (bFGF; bovine brain-derived, purified product; R & D Inc.) and a sustained release pellet containing the test sample were inserted side by side into the incision so that the bFGF pellet was located on the central side in the cornea. In the control group, the bFGF pellet and a sample-free pellet were inserted into the cornea. After 10 days, the cornea was observed under a stereoscopic microscope. When the sample administration resulted in retardation or reduction of bFGF-induced angiogenesis, the sample was judged to have inhibitory activity.

The sustained release pellets were prepared in the following manner. An ethylene-vinyl acetate copolymer (Takeda Chemical Industries, Ltd.) was dissolved in dichloromethane to a concentration of 8%. A 3 $\mu$l portion of the solution was air-dried on a glass dish, an aqueous solution of bFGF (250 ng) was then placed thereon and air-dried and, finally 3 $\mu$l of the above ethylene-vinyl acetate copolymer solution was placed further thereon and air-dried to give a sandwich sheet. This sandwich sheet was made round into a bFGF pellet. The test sample pellets were prepared by dissolving each sample in ethanol in a concentration of 20 $\mu$g/2 $\mu$l, mixing the solution with 6 $\mu$l of an ethylene-vinyl acetate copolymer solution, air-drying the mixed solution in a glass dish and making the thus-obtained sheet round.

In the Table 1 below, the inhibitory rate means the number of rats on which angiogenesis inhibitory activity was observed relative to the number of rats tested.

TABLE 1

| Angiogenesis inhibitory activity | | |
|---|---|---|
| Example No. | Inhibitory Rate | Judgment |
| 2 | 5/8 | ± |
| 3 | 3/6 | ± |
| 5 | 4/7 | ± |
| 6 | 3/4 | + |
| 7 | 7/7 | + |
| 8 | 6/7 | + |
| 9 | 5/5 | + |
| 10 | 2/5 | ± |
| 11 | 8/8 | + |
| 13 | 6/6 | + |
| 14 | 5/5 | + |
| 16 | 4/8 | ± |
| 19 | 4/6 | ± |
| 20 | 3/7 | ± |

EXPERIMENTAL EXAMPLE 2

Evaluation of inhibition of human umbilical vein endothelial cell growth

Human umbilical vein endothelial cells were isolated by perfusion of an umbilical vein with a trypsin-containing medium. The cells were cultured in sequence in GIT medium (Nihon Pharm. In.) supplemented with 2.5% fetal bovine serum and 2.0 ng/ml or recombinant human fibroblast growth factor (hereinafter simply referred to rFGF, prepared at Biotechnology Research Laboratories, Takeda Chemical Industries, Ltd.).

A suspension of human vein endothelial cells at the cell density of $2\times10^3$ (100 $\mu$l) was seeded on 96-well incubation plate (Nunc, 1-67008), and incubation was conducted in a gas-controlled thermostat vessel. The following day, 100 $\mu$l of medium containing rFGF (2 ng/ml at the final concentration) and samples of various concentrations were added.

The samples were dissolved in dimethylsulfoxide (DMSO) and then diluted with culture medium so that the final DMSO concentration did not exceed 0.25%. After 5-day culture, the medium was removed by suction, 100 $\mu$l of 1 mg/ml of MTT solution [3-(4,5-dimethyl-2-thiazolyl)-2,5-diphenyl-2H-tetrazolium bromide was dissolved in the medium] was added and kept warming for 4 hours. Then, 100 $\mu$l of a 10% SDS solution (aqueous solution of sodium dodecyl sulfate) was added, and the mixture was kept warming for 5-6 hours. The cells and MTT pigment were solubilized, and the optical density (590 μm) was measured using a spectrophotometer. The OD value of the control group to which no test sample was added was set as 100%, and the activity of each test sample for inhibiting endothelial cell growth was shown in Table 2 by the concentration of the test compound giving 50% OD value, i.e. $IC_{50}$ value.

TABLE 2

Activity of inhibiting endothelial cell growth

| Example No. | $IC_{50}$ (ng/ml) |
| --- | --- |
| 1 | 7.92 |
| 3 | 3.21 |
| 5 | 0.06 |
| 6 | 7.04 |
| 7 | 0.17 |
| 8 | 0.2 |
| 9 | 0.057 |
| 10 | 8.13 |
| 11 | 0.34 |
| 12 | 1.16 |
| 13 | 0.10 |
| 14 | 0.14 |
| 16 | 9.49 |

EXAMPLES

By the following examples, the present invention will be described in more detail, but the present invention is by no means limited to these examples.

The elution in the column chromatography in the following examples (bracketed terms are solvents used for elution) was conducted under observation by means of thin layer chromatography (TLC). In the TLC observation, as the TLC plate, Kieselgel 60F$_{250}$ (70 to 230 mesh, Merck) was employed, as the method of detection, a UV detector, a color-development method with phosphorus molybdate, etc. were employed. As the silica gel for the column, Kieselgel 60 (60 to 230 mesh, Merck) was employed. NMR spectrum shows proton NMR($^1$H-NMR), and, as interior or exterior standard tetramethylsilane was employed, and the measurement was carried out by using Gemini 200 (VARIAN) showing the δ value in terms of ppm.

Abbreviations used in the examples are as follows.

s : singlet, br : broad, d : doublet, dd : double doublet, ddd : doublet doublet doublet, t : triplet, q quartet, m : multiplet, ABq : AB quartet, J : coupling constant, Hz : Hertz, CDCl$_3$ : heavy chloroform, d$_6$-DMSO : heavy dimethyl sulfoxide, % : weight %

In the examples, "room temperatures" means temperatures ranging form about 15° to 25° C. Melting points and temperatures are all shown by centigrade.

EXAMPLE 1

6α-Amino-desoxyfumagillol (1)

In methanol (15 ml) were dissolved 6-oxo-6-desoxyfumagillol(4-(1,2-epoxy-1,5-dimethyl-4-hexenyl)-5-methoxy-1-oxaspiro[2,5]octan-6-one : 0.50 g) and ammonium acetate (1.4 g). To the solution was added sodium cyanoborohydride (0.11 g), and the mixture was stirred for one hour. The solvent was distilled off under reduced pressure, and the residue was dissolved in ethyl acetate (100 ml). The solution was washed with a saturated aqueous solution of sodium hydrogencarbonate and a saturated aqueous solution of sodium chloride, which was then dried, and the solvent was distilled off under reduced pressure. The residue was purified by means of a silica gel column chromatography (developing solvent : chloroform-methanol-conc. ammoniacal water=20:1:0.1) to afford 6α-amino-6-desoxyfumagillol (0.20 g).

NMR spectrum (CDCl$_3$, δ value) : 1.05(1H,m), 1.24(3H,s), 1.66(3H,s), 1.75(3H,s), 1.80(1H,m), 1.97(1H,d,10Hz), 2.08 to 2.47(3H,m), 2.51(1H,d,4Hz), 2.59(1H,t,6Hz), 2.90(1H,d,4Hz), 3.44(3H,s), 3.60(1H,dd,3Hz,10Hz), 3.66(1H,m), 5.21(1H,m).

EXAMPLE 2

6α-Phenylamino-6-desoxyfumagillol (2)

6-Oxo-6-desoxyfumagillol (0.30 g), aniline (0.11 ml) and acetic acid (0.12 ml) were dissolved in methanol (10 ml). To the solution was added Molecular Sieves 3A (0.20 g). To the mixture was added sodium cyanoborohydride (67 mg), which was stirred for one hour. The solvent was distilled off under reduced pressure, and the residue was dissolved in ethyl acetate (50 ml). The solution was washed with a saturated aqueous solution of sodium hydrogencarbonate and a saturated aqueous solution of sodium chloride. The solution was dried over anhydrous magnesium sulfate, and the solvent was distilled off under reduced pressure. The residue was purified by means of a silica gel column chromatography (developing solvent : ethyl acetate - hexane=1:9) to give 6α-phenylamino-6-desoxyfumagillol (0.20 g).

NMR spectrum (CDCl$_3$, δ value) : 1.25(1H,m), 1.31(3H,s), 1.66(3H,s), 1.75(3H,s), 1.80(3H,s), 1.80 to 2.47(6H,m), 2.55(1H,d,4Hz), 2.66(1H,t,6Hz), 2.88(1H,d,4Hz), 3.44(3H,s), 3.78(1H,dd,3Hz,10Hz), 4.02(1H,m), 5.21(1H,m), 6.73(3H,m), 7.19(2H,m).

EXAMPLE 3

N,N-6α-(Acetyl)methylamino-6-desoxyfumagillol(3)

6-Oxo-6-desoxyfumagillol (0.30 g), methylamine (40% methanol solution : 1.4 ml) and acetic acid (1.1 ml) were dissolved in methanol (15 ml). To the solution was added sodium cyanoborohydride (0.11 g), and the mixture was stirred for 2 hours. The solvent was distilled off under reduced pressure. The residue was dissolved in chloroform (50 ml), which was washed with a saturated aqueous solution of sodium hydrogencarbonate. The solution was dried over anhydrous magnesium sulfate, then the solvent was distilled off under reduced pressure. The residue was dissolved in dichloromethane (2 ml), to which were added pyridine (0.26 ml) and anhydruos acetic acid (0.30 ml). The mixture was stirred for 20 minutes, which was diluted with ethyl acetate (30 ml), followed by washing with a saturated aqueous solution of sodium chloride. The resultant solution was dried over anhydrous magnesium sulfate, then the solvent was distilled off under reduced pressure. The residue was purified by means of a silica gel column chromatography (developing solvent : ethyl acetate) to give N,N-6α-(Acetyl)methylamino-6-desoxyfumagillol (0.34 g).

NMR spectrum (CDCl$_3$, δ value) : 1.28(1H,m), 1.52(3H,s), 1.65(3H,s), 1.73(3H,s), 1.50 to 1.90(3H,m), 2.00 to 2.86(7H,m), 2.95(0.9H,s), 3.01(2.1H,s), 3.20 to 3.30(4H,m), 4.20(0.3H,m), 4.68(0.7H,m), 5.08 to 5.30(1H,m).

EXAMPLE 4

N,N-6α-(Acetyl-3-methylthiopropylamino)-6-desoxyfumagillol (4)

In substantially the same manner as Example 3, the compound 4 was obtained.

NMR spectrum (CDCl$_3$, δ value) : 1.28(1H,m), 1.50(1.5H,s), 1.51(1.5H,s), 1.65(3H,s), 1.73(3H,s), 1.60 to 1.90(3H,m), 2.00 to 2.86(14H,m), 3.25(3H,s), 3.19 to 3.65(3H,m), 4.20(0.5H,m), 4.68(0.5H,m), 5.08 to 5.30(1H,m).

EXAMPLE 5

6α-Acetylamino-6-desoxyfumagillol (5)

6-Oxo-6-desoxyfumagillol (0.30 acetate (0.8 g) were dissolved in methanol (10 ml). To the solution was added sodium cyanoborohydride (67 mg), which was stirred for one hour. The solvent was distilled off under reduced pressure, and the residue was dissolved in ethyl acetate (50 ml). The solution was washed with a saturated aqueous solution of sodium hydrogencarbonate and a saturated aqueous solution of sodium chloride, followed by drying over anhydrous magnesium sulfate. The solvent was distilled off under reduced pressure, and the residue was dissolved in dichloromethane (2 ml). To the solution were added pyridine (0.26 ml) and anhydrous acetic acid (0.30 ml). The mixture was stirred for 30 minutes, which was diluted with ethyl acetate (50 ml). The resultant was washed with a saturated aqueous solution of sodium chloride, a saturated aqueous solution of sodium hydrogencarbonate, and further a saturated aqueous solution of sodium chloride. The resultant was dried over anhydrous magnesium sulfate, and the solvent was distilled off under reduced pressure. The residue was purified by means of a silica gel column chromatography (developing solvent : chloroform-methanol-conc. aqueous ammonia=30:1:0.1) to afford 6α-acetylamino-6-desoxyfumagillol (0.31 g).

NMR spectrum (CDCl$_3$, δ value) : 1.28(3H,s), 1.32(1H,m), 1.66(3H,s), 1.74(3H,s), 1.60 to 1.90(3H,m), 2.00(3H,s), 2.00 to 2.47(3H,m), 2.54(1H,d,4Hz), 2.66(1H,t,6Hz), 2.85(1H,d,4Hz), 3.84(3H,s), 3.70(1H,dd,4Hz,9Hz), 4.46(1h,M), 5.20(1h,M), 5.79(1h,M).

EXAMPLE 6

6α-(p-Toluenesulfonylamino)-6-desoxyfumagillol(6)

6-Oxo-6-desoxyfumagillol (0.20 g) and ammonium acetate (0.6 g) were dissolved in methanol (10 ml). To the solution was added sodium cyanoborohydride (45 mg), and the mixture was stirred for one hour. The solvent was distilled off under reduced pressure, and the residue was dissolved in chloroform (2 ml), to which was added a saturated aqueous solution of sodium hydrogencarbonate (1 ml). To the mixture was added p-toluenesulfonyl chloride (93 mg), which was stirred for 30 minutes, followed by adding water to suspend the reaction. The reaction product was extracted with chloroform, and the extract solution was washed with a saturated aqueous solution of sodium chloride. The resultant was dried over anhydrous magnesium sulfate, then the solvent was distilled off under reduced pressure. The residue was purified by means of a silica gel column chromatography (developing solvent : ethyl acetate - hexane=1:2) to obtain 6α-(p-toluenesulfonylamino)-6-desoxyfumagillol (0.19 g).

NMR spectrum (CDCl$_3$, δ value) : 1.17(3H,s), 1.18(1H,m), 1.65(3H,s), 1.75(3H,s), 1.60 to 1.80(3H,m), 2.00 to 2.47(3H,m), 2.44(3H,s), 2.53(1H,d,4Hz), 2.55(1h,t,6Hz), 2.86(1H,d,4Hz), 3.92(3H,s), 3.50(1H,dd,4Hz,10Hz), 3.62(1H,m), 4.83(1H,m), 5.27(1H,m), 7.33(2H,d,8Hz), 7.79(2H,d,8Hz).

EXAMPLE 7

6α-(Isobutyloxycarbonylamino)-6-desoxyfumagillol (7)

In substantially the same manner as Example 6, the compound 7 was obtained.

NMR spectrum (CDCl$_3$, δ value) : 0.91(3H,s), 0.95(3H,s), 1.29(3H,s), 1.32(1H,m), 1.66(3H,s), 1.74(3H,s), 1.60 to 2.00(4H,m), 2.00 to 2.47(3H,m), 2.54(1H,d,4Hz), 2.65(1H,t,6Hz), 2.84(1H,d,4Hz), 3.40(3H,s), 3.68(1H,dd,4Hz,9Hz), 3.84(2H,d,7Hz), 4.22(1H,m), 5.04(1H,m), 5.20(1H,m).

EXAMPLE 8

6α-Benzoylamino-6- desoxyfumagillol (8)

In substantially the same manner as Example 6, the compound 8 was obtained.

NMR spectrum (CDCl$_3$, δ value) : 1.35(3H,s), 1.51(1.51(1H,m), 1.66(3H,s), 1.75(3H,s), 1.60 to 1.80(3H,m), 2.10 to 2.47(3H,m), 2.57(1H,d,4Hz), 2.74(1H,t,6Hz), 2.85(1H,d,4Hz), 3.41(3H,s), 3.79(1H,dd,4Hz,8Hz), 4.63(1H,m), 4.83(1H,m), 5.22(1H,m), 6.44(1H,m), 7.45(2H,d,8Hz), 7.78(2H,d,8Hz).

EXAMPLE 9

6α-(N'-chloroacetylureido)-6-desoxyfumagillol (9)

6-Oxo-6-desoxyfumagillol (0.50 g) and ammonium acetate (1.4 g) were dissolved in methanol (15 ml). To the solution was added sodium cyanoborohydride (0.11 mg), and the mixture was stirred for one hour. The solvent was distilled off under reduced pressure. The residue was dissolved in ethyl acetate (50 ml), and the solution was washed with a saturated aqueous solution of sodium hydrogencarbonate and a saturated aqueous solution of sodium chloride. The resultant was dried over anhydrous magnesium sulfate, then the solvent was distilled off under reduced pressure. The residue was dissolved in dichloromethane (5 ml). To the solution was added dropwise chloroacetylisocyanate (0.3 ml) at 0° C. The mixture was stirred at the same temperature for 30 minutes, which was diluted with ethyl acetate (50 ml), followed by washing with a saturated aqueous solution of sodium hydrogencarbonate and a saturated aqueous solution of sodium chloride. The resultant was dried over anhydrous magnesium sulfate, then the solvent was distilled off under reduced pressure. The residue was purified by means of a silica gel column chromatography (developing solvent : ethyl acetate - hexane=1:1) to afford 6α-(N'-chloroacetylureido)-6-desoxyfumagillol (0.42 g). (0.42 g).

NMR spectrum (CDCl$_3$, δ value) : 1.31(3H,s), 1.32(1H,m), 1.45 to 2.00(4H,m), 1.66(3H,s), 1.75(3H,s), 2.10 to 2.47(2H,m), 2.55(1H,d,4Hz), 2.68(1H,t,6Hz), 2.84(1H,d,4Hz), 3.43(3H,s), 3.63(1H,dd,4Hz,8Hz), 4.12(2H,s), 4.57(1H,m), 5.20(1H,m).

EXAMPLE 10

6α-[N'-(1-naphthyl)thioureido]-6-desoxyfumagillol (10)

In substantially the same manner as Example 9, the compound 10 was obtained.

NMR spectrum (CDCl₃, δ value) : 1.20(1H,m), 1.41(3H,s), 1.38(1H,d,2Hz), 1.55 to 1.75(1H,m), 1.65(3H,s), 1.74(3H,s), 1.85 to 2.50(4H,m), 2.42(1H,d,5Hz), 2.47(1H,d,5Hz), 2.83(1H,t,6Hz), 2.93(3H,s), 3.52(1H,m), 4.76(1H,m), 5.20(1H,m), 6.10(1H,m), 7.42 to 7.65(4H,m), 7.80 to 8.05(4H,m).

EXAMPLE 11

6α-[N'-(1-naphthyl)ureido]-6-desoxyfumagillol (11)

In substantially the same manner as Example 9, the compound 11 was obtained.

NMR spectrum (CDCl₃, δ value) : 1.26(3H,s), 1.30 to 1.85(4H,m), 1.63(3H,s), 1.73(3H,s), 2.00 to 2.47(3H,m), 2.48(1H,d,4Hz), 2.61(1H,t,6Hz), 2.73(1H,d,4Hz), 3.27(3H,s), 3.65(1H,dd,4Hz,8Hz), 4.43(1H,m), 5.17(1H,m), 5.39(1H,m), 7.02(1H,m), 7.50(3H,m), 7.71(2H,m), 7.87(1H,m), 8.04(1H,m).

EXAMPLE 12

6α-[N'-(2-chloroethyl)ureido]-6-desoxyfumagillol (12)

In substantially the same manner as Example 9, the compound 12 was obtained.

NMR spectrum (CDCl₃, δ value) : 1.20(1H,m), 1.28(3H,s), 1.65(3H,s), 1.74(3H,s), 1.60 to 1.98(3H,m), 2.10 to 2.45(3H,m), 2.53(1H,d,4Hz), 2.54(1H,t,6Hz), 2.84(1H,d,4Hz), 3.37(3H,s), 3.40 to 3.70(4H,m), 3.72(1H,dd,4Hz,10Hz), 4.31(1H,m), 5.10 to 5.42(3H,m).

EXAMPLE 13

6α-Ureido-6-desoxyfumagillol (13)

The compound 9 (0.17 g) was dissolved in tetrahydrofuran (THF, 2 ml). To the solution was added sodium N-methyl dithiocarbamate (0.11 g), and the mixture was stirred for 15 minutes. The reaction mixture was diluted with ethyl acetate (30 ml), which was washed with a saturated aqueous solution of sodium hydrogencarbonate and a saturated aqueous solution of sodium chloride. The resultant was dried over anhydrous magnesium sulfate, then the solvent was distilled off under reduced pressure. The residue was purified by means of a silica gel column chromatography (developing solvent : chloroform - methanol - conc. ammoniacal water=20:1:0.1), followed by recrystallization from benzene to give 6α-ureido-6-desoxyfumagillol (86 mg), m.p. 124° to 125° C.

NMR spectrum (CDCl₃, δ value) : 1.23(1H,m), 1.26(3H,s), 1.65(3H,s), 1.65(3H,s), 1.78(3H,s), 1.65 to 1.96(3H,m), 2.10 to 2.45(3H,m), 2.54(1H,d,4Hz), 2.59(1H,t,6Hz), 2.85(1H,d,4Hz), 3.93(3H,s), 3.71(1H,dd,4Hz), 4.32(1H,m), 4.58(2H,m), 5.19(2H,m).

EXAMPLE 14

6β-(N'-chloroacetylureido)-4',5'-dihydro-6-desoxyfumagillol (14)

The compound 9 (0.30 g) was dissolved in methanol (10 ml). To the solution was added 10% palladium-carbon (30 mg), and the mixture was stirred for one hour under hydrogen atmosphere. The catalyst was filtered off, then the solvent was distilled off under reduced pressure. The residue was purified by means of a silica gel column chromatography (developing solvent : ethyl acetate - hexane=1:2) to afford 6β-(N'-chloroacetylureido)-4',5'dihydro-6-desoxyfumagillol (0.19 g).

NMR spectrum (CDCl₃, δ value) : 0.89(3H,s), 0.82(3H,s), 1.30(3H,s), 1.20 to 1.70(1H,m), 1.93(2H,m), 2.59(1H,d,4Hz), 2.65(1H,dd,5Hz,7Hz), 2.75(1H,d,4Hz), 3.43(3H,s), 3.63(1H,dd,4Hz,8Hz), 4.12(2Hz), 4.54(1H,m).

EXAMPLE 15

6β-Phthalimido-6-desoxyfumagillol (15)

In tetrahydrofuran (THF, 30 ml) were dissolved fumagillol (1.0 g), triphenylphosphine (1.22 g) and phthalimide (0.57 mg). To the solution was added dropwise a solution of diethyl azodicarboxylate (0.88 g) in THF (5 ml), and the mixture was stirred for 30 minutes. The reaction mixture was diluted with ethyl acetate (100 ml), followed by washing with a saturated aqueous solution of sodium chloride, then with a saturated aqueous solution of sodium hydrogencarbonate and further with a saturated aqueous solution of sodium chloride. The resultant was dried over anhydrous magnesium sulfate, then the solvent was distilled off under reduced pressure. The residue was purified by means of a silica gel column chromatography (developing solvent : ethyl acetate - hexane=1:3) to afford 6β-phthalimido- 6-desoxyfumagillol (0.99 g).

NMR spectrum (CDCl₃, δ value) : 1.27(1H,m), 1.32(3H,s), 1.65 to 2.70(7H,m), 1.67(3H,s), 1.73(3H,m), 2.58(1H,d,4Hz), 2.99(1H,d,4Hz), 3.33(3H,s), 4.36(1H,t,10Hz), 5.23(1H,m), 7.73(2H,m), 7.88(2H,m).

EXAMPLE 16

6β-Amino-6-desoxyfumagillol (16)

The compound 15 (2.0 g) was dissolved in methanol (40 ml). To the solution was added hydrazine-hydrate (1.4 g), and the mixture was stirred for 20 minutes. The solvent was distilled off under reduced pressure. The residue was subjected to azeotropic distillation with ethanol to eliminate excess amount of the hydrazine-hydrate. The residue was dissolved in water (20 ml), to which was added acetic acid (1.5 ml). The mixture was stirred overnight. The precipitates were filtered off. To the filtrate was added a conc. ammoniacal water (4 ml), and the reaction product was extracted with chloroform. The extract solution was dried over anhydrous magnesium sulfate. The solvent was distilled off, and the residue was purified by means of a silica gel column chromatography (developing solvent : chloroform - methanol - conc. ammoniacal water=30:1:0.03) to afford 6β-amino-6-desoxyfumagillol (0.90 g).

NMR spectrum (CDCl₃, δ value) : 1.17(1H,m), 1.29(3H,s), 1.50 to 1.95(4H,m), 1.66(3H,s), 1.79(3H,m), 2.27(1H,m), 2.37(1H,m), 2.52(1H,d,4Hz), 2.55(1H,t,6Hz), 2.90(1H,m), 2.92(1H,d,4Hz), 3.47(1H,dd,9Hz,11Hz), 3.56(3H,s), 5.22(1H,m).

EXAMPLE 17

6β-Benzyloxycarbonylamino-6-desoxyfumagillol (17)

The compound 16 (0.50 g) and triethylamine (10 ml) were dissolved in dichloromethane (10 ml). To the solution was added dropwise at 0° C. benzyloxycarbonylchloride (0.51 ml). The mixture was stirred for one hour at the same temperature. The reaction mixture was diluted with ethyl acetate (50 ml), which was washed with a saturated aqueous solution of sodium chloride. The resultant was dried over magnesium sulfate, then the solvent was distilled off under reduced pressure. The residue was purified by means of a silica gel column chromatography (developing solvent : ethyl acetate - hexane=1:2) to afford 6β-benzyloxycarbonylamino-6-desoxyfumagillol (0.06 g).

NMR spectrum (CDCl$_3$, δ value) : 1.19(1H,m), 1.26(3H,s), 1.45 to 1.95(3H,m), 1.65(3H,s), 1.75(3H,m), 2.17(2H,m), 2.37(1H,m), 2.55(1H,d,4Hz), 2.57(1H,t,6Hz), 2.95(1H,d,4Hz), 3.37(3H,s), 3.60 to 3.90(2H,m), 5.13(2H,s), 5.21(1H,m).

EXAMPLE 18

6β-(N'-chloroacetylureido)-6-desoxyfumagillol (18)

The compound 16 (0.28 g) was dissolved in dichloromethane (3 ml). To the solution was added dropwise at 0° C. chloroacetyl isocyanate (0.10 ml). The mixture was stirred for 15 minutes at the temperature as it stood. The reaction mixture was then diluted with ethyl acetate (50 ml), followed by washing with a saturated aqueous solution of sodium hydrogencarbonate then with a saturated aqueous solution of sodium chloride. The resultant was dried over anhydrous magnesium sulfate, then the solvent was distilled off. The residue was purified by means of a silica gel column chromatography (developing solvent : ethyl acetate - hexane=1:1), followed by crystallization from isopropylether to afford 6β-(N'-chloroacetylureido)-6-desoxyfumagillol (0.18 g), m.p. 130° to 131° C.

NMR spectrum (CDCl$_3$, δ value) : 1.20(1H,m), 1.28(3H,s), 1.55 to 2.00(3H,m), 1.66(3H,s), 1.75(3H,m), 2.17(2H,m), 2.37(1H,m), 2.52(1H,d,4Hz), 2.58(1H,t,6Hz), 2.97(1H,d,4Hz), 3.44(3H,s), 3.79(1H,t,10Hz), 4.03(1H,m), 4.14(2H,s), 5.21(1H,m).

EXAMPLE 19

6β-Pyrrolidino-6-desoxyfumagillol (19)

The compound 16 (0.43 g) was dissolved in dimethylformamide (2 ml). To the solution were added anhydrous potassium carbonate (0.52 g) and then 1,4-dibromobutane (0.32 ml). The mixture was stirred for 7 hours. The reaction mixture was diluted with ether (50 ml), which was washed with water, a saturated aqueous solution of sodium hydrogencarbonate and, further, with a saturated aqueous solution of sodium chloride. The resultant was dried over anhydrous magnesium sulfate, then the solvent was distilled off. The residue was purified by means of a silica gel column chromatography (developing solvent : chloroform - methanol - conc. ammoniacal water=30:1:0.03) to afford 6β-pyrrolidino-6-desoxyfumagillol (0.23 g).

NMR spectrum (CDCl$_3$, δ value) : 1.27(1H,m), 1.29(3H,s), 1.50 to 2.00(7H,m), 1.57(1H,d,10Hz), 1.66(3H,s), 1.75(3H,m), 2.17(1H,m), 2.37(1H,m), 2.53(1H,d,4Hz), 2.54(1H,t,6Hz), 2.75(4H,m), 2.83(1H,m), 2.92(1H,d,4Hz), 3.55(3H,s), 3.71(1H,t,10Hz), 5.21(1H,m).

EXAMPLE 20

6β-Pyrrolidino-6-desoxyfumagillol methyl iodide (20)

The compound 19 (0.12 g) was dissolved in chloroform (1 ml). To the solution were added anhydrous potassium carbonate (49 mg) and then methyl iodide (0.5 ml). The mixture was stirred for 3.5 hours, then insolubles were filtered off. The solvent was distilled off under reduced pressure. The residue was reprecipitated with chloroform - ether to afford 6β-pyrrolidino-6-desoxyfumagillol methyl iodide (0.10 g).

NMR spectrum (CDCl$_3$, δ value) : 1.35(3H,s), 1.37(1H,m), 1.55 to 2.45(10H,m), 1.68(3H,s), 1.76(3H,m), 2.65(1H,d,4Hz), 2.72(1H,t,6Hz), 2.99(1H,d,4Hz), 3.02(3H,s), 3.40 to 4.05(5H,m), 3.57(3H,s), 4.29(1H,t,10Hz), 5.26(1H,m).

EXAMPLE 21

6β-Hexylamino-6-desoxyfumagillol (21)

The compound 16 (3.0 g), hexanal (1.4 ml) and acetic acid (1.5 ml) were dissolved in methanol (60 ml). To the solution was added sodium cyanoborohydride (0.67 g), and the mixture was stirred for one hour. The reaction mixture was diluted with ethyl acetate (100 ml), followed by washing with a saturated aqueous solution of sodium hydrogencarbonate and a saturated aqueous solution of sodium chloride. The resultant was dried over anhydrous magnesium sulfate, then the solvent was distilled off under reduced pressure. The residue was purified by means of a silica gel column chromatography (developing solvent : chloroform - methanol - conc. ammoniacal water=30:1:0.03) to afford 6β-hexylamino-6-desoxyfumagillol (2.35 g).

NMR spectrum (CDCl$_3$, δ value) : 0.89(3H,m), 1.10 to 2.35(12H,m), 1.66(3H,s), 1.74(3H,m), 2.51(1H,d,4Hz), 2.92(1H,d,4Hz), 3.50(3h,S), 3.69(1H,dd,9Hz,11Hz), 5.22(1H,m).

EXAMPLE 22

N,N-6β-(Methanesulfonyl)hexylamino-6-desoxyfumagillol (22)

The compound 21 (0.50 g) and triethylamine (0.38 ml) were dissolved in dichloromethane (5 ml). To the solution was added dropwise at 0° C. methanesulfonyl chloride (0.13 ml). The mixture was stirred for 15 minutes at the temperature as it stands. The reaction mixture was diluted with ethyl acetate (50 ml), followed by washing with a saturated aqueous solution of sodium hydrogencarbonate and a saturated aqueous solution of sodium chloride. The resultant was dried over anhydrous magnesium sulfate, then the solvent was distilled off under reduced pressure. The residue was purified by means of a silica gel column chromatography (developing solvent : ethyl acetate - hexane=1:3) to afford N,N-6β-(Methanesulfonylhexylamino)-6-desoxyfumagillol (0.12 g).

NMR spectrum (CDCl$_3$, δ value) : 0.85(3H,m), 1.31(12H,s), 1.50 to 2.00(6H,m), 1.66(3H,s), 1.75(3H,m), 2.17(1H,m), 2.56(1H,d,4Hz), 2.68(1H,t,6Hz), 2.93(1H,d,4Hz), 2.97(3H,S), 3.19(2H,m), 3.59(3H,s), 5.21(1H,m).

EXAMPLE 23

6-α-Phenoxycarbonylamino-6-desoxyfumagillol (23)

6-oxo-6-desoxyfumagillol (0.51 g) and ammonium acetate (1.43 g) were dissolved in methanol (15 ml). To the solution was added sodium cyanoborohydride (0.12 g) and stirred for 1 hour. The solvent was distilled off under reduced pressure. The residue was dissolved in ethyl acetate (70 ml), followed by washing with a saturated aqueous solution of sodium hydrogen carbonate and a saturated aqueous solution of sodium chloride. The resultant was dried over anhydrous magnesium sulfate, then the solvent was distilled off under reduced pressure. The residue was dissolved in dichloromethane (5 ml) and dimethylaminopyridine (0.44 g) was added. Phenyl chloroformate (0.43 g) was added dropwise to the solution and stirred for 1 hour. The resultant was diluted by addition of ethyl acetate (70 ml), followed by washing with an aqueous solution of 1 M citric acid, a saturated aqueous solution of sodium hydrogen carbonate and a saturated aqueous solution of sodium chloride. The resultant was dried over anhydrous magnesium sulfate, then the solvent was distilled off under reduced pressure. The residue was purified by means of a silica gel column chromatography (developing solvent : ethyl acetate-hexane=1 : 3) to obtain 6α-phenoxycarbonylamino-6-desoxyfumagillol (0.21 g).

NMR spectrum (CDCl$_3$, δ value) : 1.31(3H,s), 1.2~1.6(1H,m), 1.66(3H,s), 1.74(3H,s), 1.6~1.9(3H,m), 2.1~2.45(3H,m), 2.56(1H,d,4Hz), 2.69(1H,t,6Hz), 2.85(1H,d,4Hz), 3.44(3H,s), 3.72(1H,dd,9Hz,4Hz), 4.32(1H,m), 5.20(1H,m), 5.45(1H,brd,4Hz), 7.1~7.25(3H,m), 7.3~7.45(2H,m).

What is claimed is:

1. A compound of the formula:

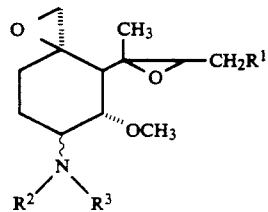

wherein
$R^1$ is 2-methyl-1-propenyl group or isobutyl group;
$R^2$ is
  (1) hydrogen atom,
  (2) a $C_{1-20}$ alkyl group which may be substituted with (i) amino, (ii) $C_{1-6}$ alkylamino, (iii) di-$C_{1-6}$ alkylamino, (iv) nitro, (v) halogen, (vi) hydroxyl, (vii) $C_{1-6}$ alkylthio, (viii) $C_{1-6}$ alkoxycarbonyl, (xiii) carboxy-$C_{1-6}$ carbamoyl, (ix) carboxyl, (xii) $C_{1-6}$ alkoxycarbonyl, (xiii) carboxy-$C_{1-6}$ alkoxy, (xiv) phenyl which may be substituted by (a) $C_{1-6}$ alkyl, (b) $C_{1-6}$ alkoxy, (c) halogen, (d) halogenated alkyl or (e) nitro, or
  (3) a $C_{6-12}$ aryl group which may be substituted with (i) $C_{2-6}$ alkyl, (ii) amino, (iii) halogen, (iv) hydroxyl, (v) $C_{1-6}$ alkoxy, (vi) cyano, (vii) carbamoyl or (viii) carboxyl;
$R^3$ is
  (1) hydrogen atom,
  (2) a $C_{1-20}$ alkyl group which may be substituted with (i) amino, (ii) $C_{1-6}$ alkylamino, (iii) di-$C_{1-6}$ alkylamino, (iv) nitro, (v) halogen, (vi) hydroxyl, (vii) $C_{1-6}$ alkylthio, (viii) $C_{1-6}$ alkoxy, (ix) cyano, (x) carbamoyl, (xi) carboxyl, (xii) $C_{1-6}$ alkoxycarbonyl, (xiii) carboxy-$C_{1-6}$ alkoxy, (xiv) phenyl which may be substituted by (a) $C_{1-6}$ alkyl, (b) $C_{1-6}$ alkoxy, (c) halogen, (d) halogenated alkyl or (e) nitro, or (xv) a 5- to 6-membered aromatic heterocyclic group containing 1 to 4 hetero atoms selected from nitrogen, oxygen and sulfur, and the said alkyl group may be epoxidated at an optional position,
  (3) a $C_{2-20}$ alkanoyl group which may be substituted with (i) amino, (ii) $C_{1-6}$ alkylamino, (iii) di-$C_{1-6}$ alkylamino, (iv) nitro, (v) halogen, (vi) hydroxyl, (vii) $C_{1-6}$ alkylthio, (viii) $C_{1-6}$ alkoxy, (ix) cyano, (x) carbamoyl, (xi) carboxyl, (xii) $C_{1-6}$ alkoxycarbonyl, (xiii) carboxy-$C_{1-6}$ alkoxy, (xiv) phenyl which may be substituted by (a) $C_{1-6}$ alkyl, (b) $C_{1-6}$ alkoxy, (c) halogen, (d) halogenated alkyl or (e) nitro, or (xv) a 5- to 6-membered aromatic heterocyclic group containing 1 to 4 hetero atoms selected from nitrogen, oxygen and sulfur,
  (4) a $C_{6-10}$ aroyl group which may be substituted with (i) $C_{2-6}$ alkyl, (ii) amino, (iii) halogen, (iv) hydroxyl, (v) $C_{1-6}$ alkoxy, (vi) cyano, (vii) carbamoyl or (viii) carboxyl,
  (5) carbamoyl group which may be substituted with Ii) $C_{1-6}$ alkyl, (ii) $C_{1-6}$ alkanoyl, (iii) halogeno-$C_{1-6}$ alkanoyl, (iv) $C_{1-6}$ alkoxycarbonylmethyl, (v) carboxymethyl, (vi) phenyl which may be substituted by (a) $C_{1-6}$ alkyl, (b) $C_{1-6}$ alkoxy, (c) halogen, (d) halogenated alkyl or (e) nitro, (vii) naphthyl, (viii) benzoyl, (ix) naphthoyl or (x) substituents forming cyclic amino group, taken together with the nitrogen atom of the carbamoyl group,
  (6) benzenesulfonyl group which may be substituted with (i) $C_{1-6}$ alkyl or (ii) halogen,
  (7) a $C_{1-6}$ alkylsulfonyl group which may be substituted with the same substituents(s) as those of substituted $C_{2-20}$ alkanoyl group mentioned in above (3),
  (8) thiocarbamoyl group which may be substituted with the same substituents(s) as those of a substituted carbamoyl group mentioned in above (5),
  (9) a $C_{1-6}$ alkoxycarbonyl group which may be substituted with the same substituent(s) as those of a substituted $C_{2-20}$ alkanoyl group mentioned in above (3),
  (10) phenoxycarbonyl group which may be substituted with the same substituent(s) as those of a substituted benzenesulfonyl group mentioned in above (6), or
  (11) a 5- or 6-membered aromatic heterocyclic carbonyl group containing 1 to 4 hetero atoms selected from nitrogen, oxygen and sulfur which may be substituted with the same substituent(s) as those of a substituted $C_{6-10}$ aroyl group mentioned in above (4), wherein said aromatic heterocyclic carbonyl group is selected from the group consisting of 2-furoyl, 2-thenoyl, nicotinoyl and isonicotinoyl;

$R^2$ and $R^3$ may form pyrolidine, piperidine or isoindoline ring which may be substituted with $C_{1-3}$ alkyl or oxo; and the bonding mark ~ represents an α-linkage or β-linkage, or a salt thereof.

2. The compound as claimed in claim 1, wherein $R^1$ is 2-methyl-1-propenyl group.

3. The compound as claimed in claim 1, wherein $R^2$ is hydrogen; $C_{1-6}$ alkyl which may be substituted with phenyl or naphthyl.

4. The compound as claimed in claim 1, wherein $R^3$ is hydrogen; $C_{2-8}$ alkanoyl which may be substituted with carboxy; benzoyl or naphthoyl which may be substituted with carboxy; carbamoyl which may be substituted with $C_{1-6}$ alkyl, $C_{1-6}$ alkanoyl, halogeno $C_{1-6}$ alkanoyl, $C_{1-6}$ alkoxycarbonylmethyl, phenyl, benzoyl or naphthoyl; benzenesulfonyl which may be substituted with $C_{1-3}$ alkyl or halogen; $C_{1-6}$ alkylsulfonyl; or thiocarbamoyl which may be substituted with $C_{1-6}$ alkyl, $C_{1-6}$ alkanoyl, halogeno $C_{1-6}$ alkanoyl, $C_{1-6}$ alkoxycarbonylmethyl, phenyl, benzoyl or naphthoyl.

5. The compound as claimed in claim 1, wherein $R^1$ is 2-methyl-1-propenyl, $R^2$ is hydrogen and $R^3$ is carbamoyl which may be substituted with halogeno $C_{1-6}$ alkanoyl.

6. The compound as claimed in claim 1, which is 6-α-(N'-chloroacetylureido)-6-desoxyfumagillol.

7. The compound as claimed in claim 1, which is 6-α-ureido-6-desoxyfumagillol.

8. A pharmaceutical composition for inhibiting angiogenesis which comprises an effective amount of the compound as claimed in claim 1 and a pharmaceutically acceptable carrier, diluent or excipient.

* * * * *